United States Patent [19]

Kohno et al.

[11] Patent Number: 5,112,836
[45] Date of Patent: May 12, 1992

[54] CYCLIC ANTHRANILILC ACID CARBOXYLIC ACID DERIVATIVES AND MEDICAL THERAPEUTIC USE THEREOF

[75] Inventors: Yasushi Kohno, Oyama; Eisuke Kojima, Koga, both of Japan

[73] Assignee: Kyorin Pharmaceutical Co., Ltd., Tokyo, Japan

[21] Appl. No.: 538,785

[22] Filed: Jun. 15, 1990

[30] Foreign Application Priority Data

Jun. 19, 1989 [JP] Japan .................... 1-156578

[51] Int. Cl.$^5$ .................... C07D 215/12; A61K 31/47
[52] U.S. Cl. .................... 514/311; 546/165
[58] Field of Search .................... 546/165; 514/311

[56] References Cited

FOREIGN PATENT DOCUMENTS 139412  4/1930  Switzerland .................... 546/165

*Primary Examiner*—David B. Springer
*Attorney, Agent, or Firm*—Oblon, Spivak, McClelland, Maier & Neustadt

[57] ABSTRACT

Cyclic anthranilic acid carboxylic acid derivatives of the following formula,

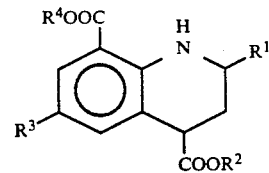

wherein $R^1$ is hydrogen atom, carboxyl group, lower alkoxy carbonyl group having 1 to 3 carbon atoms, or phenyl group which may be substituted, $r^2$ and $R^4$ are each independently a hydrogen atom, lower alkyl group having 1 to 3 carbon atoms or benzyl group, $R^3$ is a hydrogen atom, halogen atom, nitro group, amino group, cyano group, carbamoyl group, carboxyl group, lower alkanoylamino group having 1 to 4 carbon atoms, benzoylamino group, lower alkylsulfonylamino group having 1 to 3 carbon atoms or phenylsulfonylamino group which may be substituted by methyl group; the acid addition or alkali salts thereof, are useful as drugs treat autoimmune diseases, antirheumatic agents and therapeutic or prophylactic agents to treat metabolic bone diseases.

6 Claims, No Drawings

CYCLIC ANTHRANILILC ACID CARBOXYLIC ACID DERIVATIVES AND MEDICAL THERAPEUTIC USE THEREOF

DETAILED DESCRIPTION OF THE INVENTION

This invention is concerned with certain novel cyclic anthranilic acid carboxylic acid derivatives, their acid or alkali slats thereof and the process for their preparation thereof. This invention is also concerned with the use of these novel compounds as antirheumatic agents, drugs for treating autoimmune diseases, and drugs which have both therapeutic and prophylactic effects on metabolic bone diseases.

Chronic diseases related to immune responses include rheumatoid arthritis and other autoimmune diseases (systemic lupus erythematosus, psoriatic arthritis, atopic dermatitis, ankylosing spondylitis). These diseases are considered to be caused by bacteria, virus or autoantigens or by an aberration in cytokine regulation of T cells. Especially, patients with rheumatoid arthritis demonstrate various immune abnormalities including reduced functions of suppressor T cells and hyperactivity of B cells.

Non-steroidal antiinflammatory drugs are widely used as first choice drugs in the therapy of rheumatoid arthritis and other diseases due to immunological disorders. While these drugs offer symptomatic relief for patients with these diseases, they fail to alter the underlying immunological dysfunction or the overall course of the disease process. Furthermore, serious side effects from prolonged use of these drugs also have been well documented.

On the other hand, second choice antirheumatic drugs, such as gold salt and D-penicillamine have little acute anti-inflammatoy effects, but they appear to slow or halt the tissue destruction and more especially the progression of articular damage. They also have immunomodulatory effects. However, it is necessary to improve the safety and other aspects of these drugs, because of the higher incidence of side effects that have been observed in 40-50% of the patients treated with these drugs.

Metabolic bone diseases as generic term include osteoporosis, osteomalacia and ostetic fibrous. In patients with the diseases, there are morbid changes in weight, constitution and structure of bone as a result of the failure of the systemic bone formation and resorption process. This is caused by abnormalities in the somatological regulatory system due to various hormones or vitamins and by congenital or acquired abnormalities of the functions of the osteocytes. It is also associated with abnormal calcium and phosphorus metabolism. Vitamin D, calcium, calcitonin and phosphorus are used as therapeutic drugs, but their effectiveness has not been clearly proven and development of a superior drug has been strongly desired.

As a result of our research into the development of an antirheumatic agent, we have found that novel cyclic anthranilic acid carboxylic acid derivatives represented by a general formula (I) and their acid or alkali salts thereof, have potent therapeutic effects upon adjuvant arthritis without inhibiting cyclooxygenase activity. We have proved the superiority of these compounds. We have also found that these compounds of this invention have inhibitory effects on bone damage in adjuvant arthritis.

The compound of the present invention has one or two asymmetric carbons. Therefore the present invention also comprises the compound of optical isomers and the mixture thereof.

The preparation of the compound of the present invention is illustrated as follows.

It is known that only a few of cyclic anthranilic acid derivatives were synthesized from 1,7-trimethylene isatins by oxidation with hydrogen peroxide in alkaline solution (E. Ziegler et al., Monatsh. Chem., 94, 698, (1963), ibid. 95, 59 (1964)) and from quinolinecarboxylic acid by catalytic reduction (C. Satyendranath et al., J. Annamalai Univ., 2, 227 (1933)), but their pharmacological property was not reported.

The compound of the formula (I) of the present invention can be prepared by either of the following processes (1) to (5).

Process (1): A compound of the formula (III), namely, $R^4$ is a hydrogen atom in the formula (I), can be obtained by hydrolyzing and decarbonylating a compound of the formula (II). And also the compound of the formula (III) can be prepared favorably by hydrolysis of the compound of the formula (II), followed by treating with oxidizing agent. Typically the compound of the formula (III) can be prepared by heating the compound of the formula (II) in a solution containing slight excess amount of base such as potassium hydroxide or sodium hydroxide to hydrolyze and then oxidizing with excess molar ammount of mild oxidizing agent such as hydrogen peroxide, peracetic acid or the like. The reaction is favorably carried out at a temperature between 0° C. to 50° C. for 30 minutes to 3 hours.

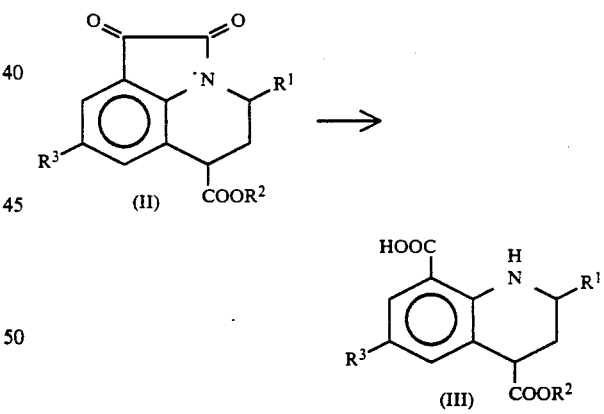

wherein $R^1$ is hydrogen atom, carboxyl group, lower alkoxy carbonyl group having 1 to 3 carbon atoms, or phenyl group which may be substituted, $R^2$ is a hydrogen atom, lower alkyl group having 1 to 3 carbon atoms or benzyl group, $R^3$ is a hydrogen atom, halogen atom, nitro group, amino group, cyano group, carbamoyl group, carboxyl group, lower alkanoylamino group having 1 to 4 carbon atoms, benzoylamino group, lower alkylsulfonylamino group having 1 to 3 carbon atoms or phenylsulfonylamino group which may be substituted by methyl group.

Process (2): A compound of the formula (V), namely, $R^3$ is amino group in the formula (I), can be prepared by reduction of a compound of the formula (IV).

It is favorable that catalytic reduction is carried out in the presence of 10% of palladium-on-charcoal in a solvent such as dimethylformamide.

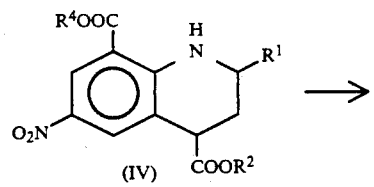

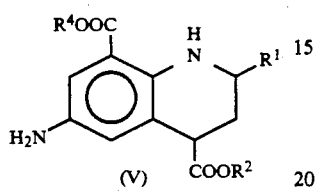

wherein $R^1$, $R^2$ and $R^4$ have the same meanings as in the formula (I).

Process (3): A compound of the formula (VII), namely, $R^3$ is alkanoylamino group having 1 to 3 carbon atoms, benzoylamino group which may be substituted, alkylsulfonylamino group having 1 to 3 carbon atoms or phenylsulfonylamino group which may be substituted in the formula (I), can be prepared by the reaction of a compound of the formula (V) with a compound of the formula (VI) in a suitable solvent such as dioxane, dimethyl sulfoxide and so on, in the presence of an acid acceptor such as triethylamine, pyridine and so on, at room temperature.

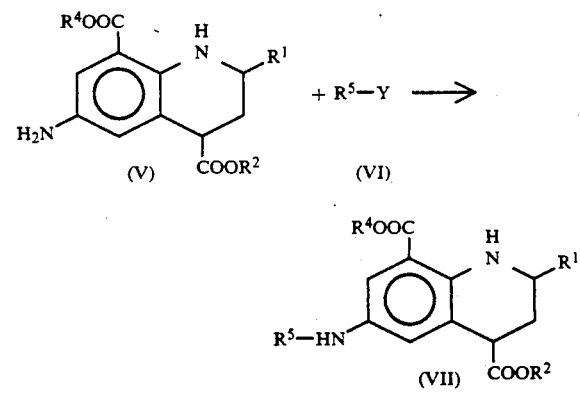

wherein $R^5$ is a lower alkanoyl group having 1 to 3 carbon atoms, benzoyl group, lower alkylsulfonyl group having 1 to 3 carbon atoms or phenylsulfonyl group which may be substituted by methyl group, Y is halogen atom, $R^1$, $R^2$ and $R^4$ have the above-stated meanings.

Process (4): A compound of the formula (IX), namely, $R^3$ is cyano group in the formula (I), can be prepared by reacting a compound of the formula (VIII) with potassium cyanide, sodium cyanide and so on in a solvent such as dimethylformamide, pyridine, N-methylpyrrolidone and so on at elevated temperature under stirring.

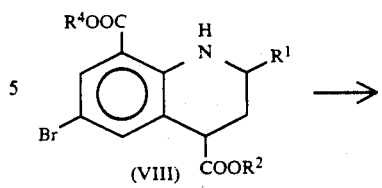

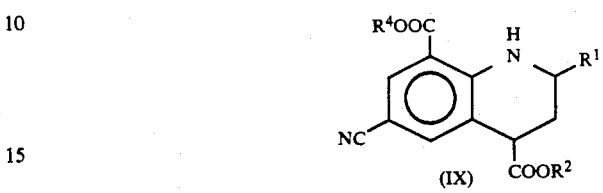

wherein $R^1$, $R^2$ and $R^4$ have the above-stated meanings.

Process (5): A compound of formula (I), namely, $R^3$ is carbamoyl group or carboxyl group in the formula (I), can be prepared by hydrolyzing a compound of formula (IX) cyano group in an appropriate solvent such as methanol, ethanol and so on containing a suitable base such as sodium hydroxide, potassium hydroxide and so on.

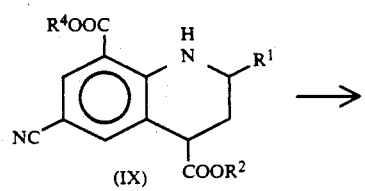

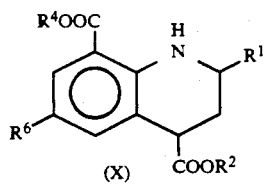

wherein $R^1$, $R^2$ and $R^4$ have the above-stated meanings, $R^6$ is carbamoyl or carboxyl group.

The starting materials, namely the compound of the formula (II), are also new and obtained by the known method (Japan Kokai, Sho 60-243088).

The compound of the formula (I) can be converted, if desired, to the salt by the usual method. Acid addition salt may be prepared using organic or inorganic acid such as hydrochloric acid, sulfuric acid, phosphoric acid, methanesulfonic acid, lactic acid, acetic acid, citric acid, tartaric acid an so on. Alkali salt of the present compound may be metal salt such as sodium, potassium and so on.

The following examples will further illustrate the invention without, however, limiting it thereto.

EXAMPLE 1

Methyl 5,6-dihydro-1,2-dioxo-4H-pyrrolo[3,2,1-ij]quinoline-6-carboxylate

A solution of methyl 1,2,3,4-tetrahydroquinoline-4-carboxylate (51.0 g) in tetrahydrofuran (THF, 200 ml) was heated under refluxing and a solution of oxalyl chloride (30 ml) in dry THF was added thereto. The mixture was refluxed for 4 hours, then cooled and concentrated. The residue was dissolved in carbon disulfide (800 ml) and aluminum chloride (66.7 g) was added portionwise. The mixture was refluxed for 4 hours, and then allowed to stand overnight. The solvent was eliminated by decantation and to the residue was added ice-water (1 litter). The mixture was extracted with chloroform. The chloroform layer was washed well with water, dried over anhydrous sodium sulfate and concentrated to give the title compound (55.15 g, 83.3%) which was recrystallized from acetonitrile to dark red crystals, mp 135° C.-136° C.

Analysis (%) for $C_{13}H_{11}NO_4$, Calcd. (Found): 63.67 (63.98); H, 4.52 (4.45); N, 5.71 (5.75).

EXAMPLE 2

Methyl 8-chloro-5,6-dihydro-1,2-dioxo-4H-pyrrolo[3,2,1-ij]-quinoline-6-carboxylate A mixture of methyl 5,6-dihydro-1,2-dioxo-4H-pyrrolo[3,2,1-ij]quinoline-6-carboxylate (Example 1; 3 g) and N-cholorsuccinimide (NCS, 1.96 g) in dimethylformamide (DMF, 30 ml) was heated at 80° C. with stirring for an hour. After cooling, the mixture was concentrated. The residue was extracted with chloroform (200 ml). Chloroform layer was washed with water, dried over anhydrous sodium sulfate and concentrated to give the title compound (3.28 g, 96.2%) which was recrystallized form acetonitrile to dark red needles, mp 132° C.-133° C.

EXAMPLE 3

Methyl 8-bromo-5,6-dihydro-1,2-dioxo-4H-pyrrolo[3,2,1-ij]-quinoline-6-carboxylate This compound was obtained by the procedure described in Example 2, but replacing the NCS with N-bromosuccinimide, with 97.3% yield, mp 150° C.-151° C.

EXAMPLE 4

Methyl 8-nitro-5,6-dihydro-1,2-dioxo-4H-pyrrolo[3,2,1-ij]-quinoline-6-carboxylate To a suspension of the compound obtained in Example 1 (16 g) in acetic anhydride-acetic acid (1:1, 300 ml) was added fuming nitric acid (5 ml) under ice-cooling with stirring. The mixture was stirred under ice-cooling for 3 hours and then at room temperature for 2 hours. Ice-water (1 litter) was added to the reaction mixture. The resulting precipitate was collected by filtration, washed with water and dried to give the title compound (17.64 g, 93.2%) which was recrystallized from acetonitrile to yellow crystals, mp 144° C.-145° C.

Analysis (%) for $C_{13}H_{12}N_2O_6$, Calcd. (Found): C, 53.80 (53.87); H, 3.47 (3.47); N, 9.65 (9.97).

Using the procedure described above, compounds shown in table 1 were prepared.

TABLE 1

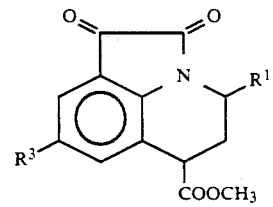

| Example | $R^1$ | $R^3$ | Yield (%) | mp (°C.) | Analysis (%) Calcd./Found |   |   |
|---|---|---|---|---|---|---|---|
|   |   |   |   |   | C | H | N |
| 5 | Ph | H | 88.1 | 187 | 71.02 | 4.71 | 4.36 |
|   |   |   |   |   | 70.72 | 4.72 | 4.36 |
| 6 | Ph | Cl | 97.5 | 216-217 | 64.14 | 3.97 | 3.94 |
|   |   |   |   |   | 64.07 | 3.98 | 4.37 |
| 7 | Ph | Br | 98.7 | 218-219 | 57.02 | 3.53 | 3.50 |
|   |   |   |   |   | 57.21 | 3.44 | 3.55 |
| 8 | Ph | $NO_2$ | 93.2 | 258-259 | 62.30 | 3.85 | 7.65 |
|   |   |   |   |   | 62.18 | 3.73 | 8.04 |

*Recrystallized solvent = acetonitrile

EXAMPLE 9

1,2,3,4-Tetrahydroquinoline-4,8-dicarboxylic acid

To a mixture of methyl 5,6-dihydro-1,2-dioxo-4H-pyrrolo-3,2,1-ij quinoline-6-carboxylate (2.5 g) and soduyn gtdrixude (4 g) in water (150 ml) was added 35% hydrogen peroxide (5 ml) and the mixture was stirred for 2 hours at room temperature and filtered off the insoluble materials. The filtrate was adjusted to pH 2 by the addition of concentrated hydrochloric acid. The resulting precipitate was collected by filtration, washed with water, and dried to give 1.42 g (62.9%) of the title compound, mp 215° C.-216° C.

Analysis (%) for $C_{11}H_{11}NO_4$, Calcd. (Found): C, 59.73 (56.69); H, 5.01 (5.04); N, 6.33 (6.20);

Using the procedure described above, compounds shown in table 2 were prepared.

TABLE 2

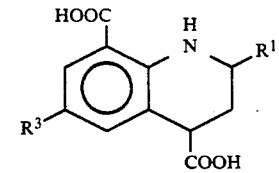

| Example | $R^1$ | $R^3$ | Yield (%) | mp* (°C.) | Analysis (%) Calcd./Found |   |   |
|---|---|---|---|---|---|---|---|
|   |   |   |   |   | C | H | N |
| 10 | H | Cl | 77.0 | 236-237(A)* | 51.68 | 3.94 | 5.48 |
|   |   |   |   |   | 51.70 | 3.85 | 5.43 |
| 11 | H | Br | 84.2 | 238-239(A) | 44.02 | 3.36 | 4.67 |
|   |   |   |   |   | 44.11 | 3.28 | 4.64 |
| 12 | H | $NO_2$ | 95.6 | 270-274(A) | 49.63 | 3.79 | 10.52 |
|   |   |   |   |   | 49.54 | 3.75 | 10.41 |
| 13 | Ph | H | 91.5 | 239-241(A) | 68.68 | 5.09 | 4.71 |
|   |   |   |   |   | 68.29 | 4.98 | 4.70 |
| 14 | Ph | Cl | 93.5 | 274-275(A) | 61.55 | 4.25 | 4.22 |
|   |   |   |   |   | 61.55 | 4.18 | 4.15 |
| 15 | Ph | Br | 87.9 | 264-265(A) | 54.27 | 3.75 | 3.72 |
|   |   |   |   |   | 54.18 | 3.58 | 3.66 |
| 16 | Ph | $NO_2$ | 96.4 | 253-254(B) | 59.65 | 4.12 | 8.18 |
|   |   |   |   |   | 59.24 | 4.13 | 8.08 |

*Recrystallized solvent = (A): acetonitrile (B): ethanol-ethyl acetate

EXAMPLE 17

6-Cyano-2-phenyl-1,2,3,4-tetrahydroquinoline-4,8-dicarboxylic acid a) Dibenzyl 6-bromo-2-phenyl-1,2,3,4-tetrahydroquinoline-4,8-dicarboxylate

A mixture of the compound obtained in Example 15 (13 g), potassium carbonate (10 g) and benzyl bromide (9.5 ml) was stirred at room temperature for 2 hours. The mixture was filtered and the filtrate was concentrated. Ethyl acetate was added to the residue. The organic layer was washed with water, dried over anhydrous sodium sulfate and concentrated to give the objective compound (19.29 g, 98.9%) as brown crystals.

b) Dibenzyl 6-cyano-2-phenyl-1,2,3,4-tetrahydroquinoline-4,8-dicarboxylate

To a solution of the above obtained compound (19.29 g) in DMF (60 ml) was added cuprous cyanide (4.13 g). The mixture was refluxed for 21 hours. After cooling, ferric chloride hexahydrate (2.0 g), concentrated hydrochloric acid (2 ml) and water (400 ml) was added thereto. The mixture was stirred at 60 °C. for 30 minutes and extracted with ethyl acetate. The organic layer was washed with 10% aqueous sodium hydroxide, water, dilute hydrochloric acid, water and saturated sodium chloride water successively, dried over anhydrous sodium sulfate and concentrated to give the residue which was purified by kiesel gel column chromatography (ethyl acetate:n-hexane=1:3) to give the objective compound (10.21 g, 61.7%) as yellow crystals.

c) 6-Cyano-7-phenyl-1,2,3,4-tetrahydroquinoline-4,8-dicarboxylic acid

To a solution of the compound obtained above (3 g) in ethanol (50 ml) was added 10% palladium-on-charcoal (350 mg). The mixture was stirred in a hydrogen atmosphere at atmospheric pressure and at room temperature for 3 hours. The solution was filtered and the filtrate was concentrated to give the title compound (1.75 g, 86.2%) which was recrystallized from ethanol to pale yellow crystals, mp 231° C.–232° C.

EXAMPLE 18

2-Phenyl-1,2,3,4-tetrahydroquinoline-4,6,8-tricarboxylic acid

A solution of the compound obtained in example 17 b) (5.6 g) and sodium hydroxide (5 g) in water (20 ml) was refluxed for 10 hours. After cooling, water (200 ml) was added and the mixture was adjusted to pH 2 by the addition of concentrated hydrochloric acid. The resulting precipitate from the mixture was collected by filtration, washed with water, dried to give the title compound (3.05 g, 76.4%) which was recrystallized from DMF-ethanol to white crystals, mp 300° C.

Analysis (%) for $C_{18}H_{15}NO_6$, Calcd. (Found): C, 63.34 (63.13); H, 4.43 (4.47); N, 4.10 (4.48).

EXAMPLE 19

6-Methanesulfonylamino-2-phenyl-1,2,3,4-tetrahydroquinoline-4,8-dicarboxylic acid a) Dimethyl 6-nitro-2-phenyl-1,2,3,4-tetrahydroquinoline-4,8-dicarboxylate

A mixture of the compound obtained in example 16 (8.92 g), potassium carbonate (10 g) and methyl iodide (5 ml) in DMF (30 ml) was stirred for 2 hours. The solution was filtered and the filtrate was concentrated. The residue was dissolved in ethyl acetate (300 ml). The organic layer was washed with water, dried over anhydrous sodium sulfate and concentrated to give 7.92 g (82.3%) of the objective compound as yellow crystals.

b) Dimethyl 6-methanesulfonylamino-2-phenyl-1,2,3,4-tetrahydroquinoline-6,8-dicarboxylate The compound obtained above (7.12 g) was converted to 6-amino derivative by the procedure of example 18. To a solution of 6-amino derivative (2.8 g) in dioxane (30 ml) was added triethylamine (1.5 ml) and methanesulfonyl chloride (0.83 ml). The mixture was stirred at room temperature for 4 hours, then after the addition of water (200 ml), extracted with ethyl acetate. The organic layer was dried over anhydrous sodium sulfate and concentrated to give the residue, which was purified by silica gel column chromatography (ethyl acetate:n-hexane=1:2) to give 3.02 g (88.0%) of the objective compound as oil.

c) 6-Methanesulfonylamino-2-phenyl-1,2,3,4-tetrahydroquinoline-6,8-dicarboxylic acid The ester obtained above (3.02 g) was converted to the objective acid (2.52 g, 89.90%) by the procedure of example 17 c). It was recrystallized from ethanol to yellow crystals, mp 223° C.–224° C.

EXAMPLE 20

Ethyl 8-bromo-5,6-dihydro-1,2-dioxo-4H-pyrrolo[3,2,1-ij]-quinoline-6-carboxylate A mixture of methyl 5,6-dihydro-1,2-dioxo-4H-pyrrolo[3,2,1-ij]quinoline-6-carboxylate (example 1, 13 g) and N-bromosuccinimide (NBS, 11.32 g) in DMF (50 ml) was heated at 80° C. with stirring for 2 hours. After cooling, the mixture was concentrated. The residue was extracted with chloroform (500 ml). Chloroform layer was washed with water, dried over anhydrous sodium sulfate and concentrated to give the title compound (16.72 g, 97.3%) which was recrystallized from acetonitrile to dark red needles, mp 150° C.–151° C.

EXAMPLE 21

6-Bromo-1,2,3,4-tetrahydroquinoline-4,8-dicarboxylic acid

To a mixture of methyl 8-bromo-5,6-dihydro-1,2-dioxo-4H-pyrrolo 3,2,1 ij quinoline-6-carboxylate (15 g) and sodium hydroxide (10 g) in water (700 ml) was added 35% hydrogen peroxide (10 ml) and the mixture was stirred for 2 hours at room temperature and filtered. The filtrate was adjusted to pH 2 by the addition of concentrated hydrochloric acid. The resulting precipitate was collected by filtration, washed with water, and dried to give 11.7 g (84.2%) of the title compound, mp 238° C.–239 ° C.

Analysis (%) for $C_{11}H_{10}BrNo_4$, Calcd. (Found): C, 44.02 (44.11); H, 3.36 (3.28); N, 4.67 (4.64).

EXAMPLE 22

2-Phenyl-6-p-toluenesulfonylamino-1,2,3,4-tetrahydroquinoline-4,8-dicarboxylic acid a) Dimethyl 6-nitro-2-phenyl-1,2,3,4-tetrahydroquinoline-4,8-dicarboxylate

A mixture of 6-nitro-2-phenyl-1,2,3,4-tetrahydroquinoline-4,8-dicarboxylic acid (8.92 g), potassium carbonate (10 g) and methyl iodide (5 ml) in DMF (30 ml) was stirred at room temperature for 2 hours, filtered and concentrated. The residue was dissolved in ethyl acetate (300 ml). The organic layer was washed with water, dried over anhydrous sodium sulfate and concentrated to give 7.92 g (82.3%) of the title compound as yellow crystals.

b) Dimethyl 6-amino-2-phenyl-1,2,3,4-tetrahydroquinoline-4,8-dicarboxylate

A mixture of the above obtained compound (7.92 g) and 10% palladium-on-charcoal (700 mg) in DMF (100 ml) was stirred in a hydrogen atmosphere at atmospheric pressure and at room temperature for 5 hours and filtered. The filtrate was concentrated to give 5.67 g (85.4%) of the title compound.

c) Dimethyl 2-phenyl-6-p-toluenesulfonylamino-1,2,3,4-tetrahydroquinoline-4,8-dicarboxylate To a solution of the above obtained compound (2.8 g) in dioxane (30 ml) was added p-toluenesulfonyl chloride (2.04 g) and triethylamine (1.5 ml) and the mixture was stirred for 4 hours at room temperature. Water (300 ml) was added thereto. The mixture was extracted with ethyl acetate. The organic layer was washed with water, dried over anhydrous sodium sulfate and concentrated to give a residue, which was purified by kiesel gel column chromatography ($SiO_2$ 250 g, ethyl acetate:n-hexane=1:2). The objective compound (3.56 g) was obtained as brown oil.

d) 2-Phenyl-6 p-toluenesulfonylamino-1,2,3,4-tetrahydroquinoline-4,8-dicarboxylic acid A mixture of the above compound (3.56 g), sodium hydroxide (2 g) in ethanol (30 ml) and water (20 ml) was refluxed for 4 hours. After cooling, to the reaction mixture was added water (100 ml), adjusted to pH 1 by adding concentrated hydrochloric acid and resulting precipitate was collected by filtration. The precipitate was washed with water and dried, which was purified by kiesel gel column chromatography ($SiO_2$ 200 g, dichloro-methane:ethanol=10:1) to give the title compound (1.35 g, 40.3%) which was recrystallized from ethanol to pale yellow crystals, mp 235° C.–237° C.

EXAMPLE 23

6-Cyano-1,2,3,4-tetrahydroquinoline-4,8-dicarboxylic acid a) Dibenzyl 6-bromo-1,2,3,4-tetrahydroquinoline-4,8-dicarboxylate

A mixture of 6-bromo-1,2,3,4-tetrahydroquinoline-4,8-dicarboxylic acid (10.2 g), benzyl bromide (9 ml) and potassium carbonate (10 g) in DMF (30 ml) was stirred at room temperature for 3 hours and filtered. To the filtrate was added a mixture of ethyl acetate-benzene (1:1, 300 ml). The mixture was washed with water, dried over anhydrous sodium sulfate and concentrated to give oily objective compound (17.44 g).

b) Dibenzyl 6-cyano-1,2,3,4-tetrahydroquinoline-4,8-dicarboxylate

A mixture of the above obtained compound (17.44 g) and cuprous cyanide (4.13 g) in DMF (50 ml) was refluxed with stirring. After cooling, ferric chloride hexahydrate (20 g), concentrated hydrochloric acid (2 ml) and water (300 ml) was added thereto. The mixture was stirred at 60° C. for an hour and extracted with ethyl acetate. The organic layer was washed with 10% aqueous sodium hydroxide solution, water, 10% hydrochloric acid and water successively, and dried over anhydrous sodium sulfate.

The solvent was distilled to give residue, which was purified by kiesel gel column chromatography ($SiO_2$ 350 g, ethyl acetate:n-hexane=1:3) to give the objective compound (11.8 g, 81.4%) as pale yellow crystals.

c) 6-cyano-1,2,3,4-tetrahydroquinoline-4.8-dicarboxylic acid

A mixture of the above obtained compound (3.5 g) and 10% palladium-on-charcoal (400 mg) in ethanol (100 ml) was stirred in hydrogen atmosphere at atmospheric pressure and at room temperature for 3 hours and filtered. The filtrate was concentrated to give residue, which was purified by kiesel gel column chromatography ($SiO_2$ 150 g, dichloromethane:ethanol=9:1) to give the title compound (1.03 g, 51%) was obtained and recrystallized from ethanol to pale yellow crystals, mp 235° C.–236° C.

Analysis (%) for $C_{12}H_{10}N_2O_4$, Calcd. (Found): C, 58.54 (58.59); H, 4.09 (4.18); N, 11.38 (11.07).

EXAMPLE 24

6-Carbamoyl-1,2,3,4-tetrahydroquinoline-4,8-dicarboxylic acid

A mixture of dibenzyl 6-cyano-1,2,3,4-tetrahydroquinoline-4.8 dicarboxylate (5 g), sodium hydroxide (4 g) in ethanol (50 ml) and water (500 ml) was refluxed for 18 hours. After cooling, water (100 ml) was added thereto. The mixture was adjusted to pH 2 by the addition of concentrated hydrochloric acid. The resulting precipitate was collected by filtration, washed with water and dried to give the title compound (1.87 g, 60.5%) which was recrystallized from DMF-ethanol to white crystals, mp 265° C.–266 ° C.

Analysis (%) for $C_{12}H_{12}N_2O_5$, Calcd. (Found): 54.55 (54.51); H, 4.58 (4.67); N, 10.60 (10.29).

EXAMPLE 25

1,2,3,4-Tetrahydroquinoline-4,6,8-tricarboxylic acid

A solution of 6-carbamoyl-1,2,3,4-tetrahydroquinoline-4,8-dicarboxylic acid (1.77 g) in 10% aqueous sodium hydroxide solution (20 ml) was refluxed for 10 hours and after cooling, adjusted to pH 1. The resulting precipitate was collected by filtration, washed with water and dried to give the title compound (1.29 g, 72.9%) which was recrystallized from ethanol to white crystals, mp 240° C.–241° C.

EXAMPLE 26

6-p-Toluenesulfonylamino-1,2,3,4-tetrahydroquinoline-4,8-dicarboxylic acid

Using the procedure described in example 22, 6-nitro-1,2,3,4-tetrahydroquinoline-4,8-dicarboxylic acid was converted to the title compound as pale yellow crystals, mp 221° C.-223° C. (Ethanol).

Analysis (%) for $C_{18}H_{18}N_2O_6S$, Calcd. (Found): C, 55.38 (55.55); H, 4.65 (4.70); N, 7.18 (7.04).

EXAMPLE 27

6-Methanesulfonylamino-1,2,3,4-tetrahydroquinoline-4,8-dicarboxylic acid

6-Nitro-1,2,3,4-tetrahydroquinoline-4,8-dicarboxylic acid was converted to the title compound as pale yellow crystals, mp 188° C.-190° C. (Ethanol) by the procedure described in example 22 and 26, but replacing the p-toluenesulfonyl chloride with methane-sulfonyl chloride.

Analysis (%) for $C_{12}H_{14}N_2O_6S$, Calcd. (Found): C, 45.86 (45.98); H, 4.49 (4.35); N, 8.91 (9.09).

The following experiments will illustrate the effectiveness of the compound of the present invention.

EXPERIMENT 1

Inhibition of Increased Vascular Permeability

Male ddy mice (6 weeks of age) were used in this experiment. Example 9 compound suspended in 5% gum arabic solution was administered p.o., 45 minutes before the i.v. injection of 1.0% Evans blue solution (0.1 ml/10 g B.W.). Immediately after the i.v. injection, 1.0% acetic acid solution was administered i.p. (0.1 ml/10 g B.W.). The mice were killed 30 minutes after the acetic acid injection. Peritoneal exudate was collected by washing out the peritoneal cavity with physiological saline and centrifuged at 3,000 r.p.m. After the centrifugation, spectrophotometry of the supernatant was measured at 630 nm. Results were expressed as dye leakage and percent inhibition.

As shown in Table 3, Example 9 compound significantly reduced increased vascular permeability induced by acetic acid in mice.

TABLE 3

| Compound | Dose (mg/kg) | N | Dye leakage (μg/ml) (mean ± S.E.) | Inhibition (%) |
|---|---|---|---|---|
| Control | — | 10 | 21.15 ± 1.41 | — |
| Example 9 | 100 | 9 | 15.53 ± 1.07* | 26.6 |

*Significantly different from control, p < 0.01.

EXPERIMENT 2

Therapeutic Effect on Adjuvant Arthritis in Sprague Dawley Rats

Adjuvant arthritis was induced by intradermal injection of heat-killed *Mycobacterium butyricum* (0.6 mg/rat) suspended in liquid paraffin into the right hind foot pad of female rats (8 weeks of age). The compounds of this invention suspended in 0.3% carboxymethylcellulose solution were orally administered once a day for 7 days during days 14 to 20 after adjuvant injection. Left hind paw volume was measured by the water immersion method.

As shown in Table 4, administration of Example 14 and 15 compounds reduced the swelling of left (uninjected) hind paw.

TABLE 4

| compound | Dose (mg/kg) | N | Increase in left hind paw[1] | | |
|---|---|---|---|---|---|
| | | | Day 17 | Day 21 | Day 27 |
| control (adjuvant) | — | 8 | 1.81 ± 0.28 | 2.22 ± 0.28 | 2.36 ± 0.31 |
| example 14 | 50 | 8 | 1.78 ± 0.30 | 1.85 ± 0.33 | 1.59 ± 0.38 |
| example 15 | 50 | 8 | 1.80 ± 0.23 | 2.07 ± 0.36 | 2.04 ± 0.45 |

[1]volume (ml), mean ± S.E.

What is claimed is:

1. A compound of the formula (I),

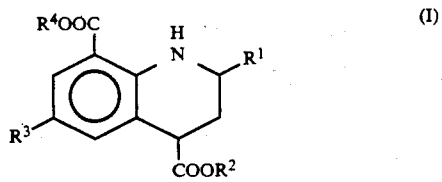

wherein $R^1$ is hydrogen atom, carboxyl group, lower alkoxy carbonyl group having 1 to 3 carbon atoms, or phenyl group which may be substituted, $R^2$ and $R^4$ are each independently a hydrogen atom, lower alkyl group having 1 to 3 carbon atoms or benzyl group, $R^3$ is hydrogen atom, halogen atom, nitro group, amino group, cyano group, carbamoyl group, carboxyl group, lower alkanoylamino group having 1 to 4 carbon atoms, benzoylamino group, lower alkylsulfonylamino group having 1 to 3 carbon atoms or phenylsulfonylamino group which may be substituted by methyl group; the acid addition or alkali salts thereof.

2. A therapeutic composition, comprising: a therapeutically effective amount of the compound of claim 1 in combination with a pharmaceutically acceptable excipient.

3. The composition of claim 2, wherein said composition is effective in the treatment of autoimmune diseases, rheumatic disease and metabolic bone disease.

4. A method of treating autoimmune diseases, comprising: administering to a subject suffering from an autoimmune disease a therapeutically effective amount of the composition of claim 2.

5. A method of treating rheumatic disease, comprising: administering to a subject suffering from rheumatic disease a therapeutically effective amount of the composition of claim 2.

6. A method of treating metabolic bone diseases, comprising: administering to a subject suffering from a metabolic bone disease the composition of claim 2.

* * * * *

UNITED STATES PATENT AND TRADEMARK OFFICE
CERTIFICATE OF CORRECTION

PATENT NO. : 5,112,836

DATED : May 12, 1992

INVENTOR(S) : Yasushi Kohno et al.

It is certified that error appears in the above-identified patent and that said Letters Patent is hereby corrected as shown below:

On the title page, item (54) should read --CYCLIC ANTHRANILIC ACID CARBOXYLIC ACID DERIVATIVES AND MEDICAL THERAPEUTIC USE THEREOF--

Signed and Sealed this

Sixth Day of July, 1993

Attest:

MICHAEL K. KIRK

Attesting Officer

Acting Commissioner of Patents and Trademarks